(12) United States Patent
Hirano et al.

(10) Patent No.: US 10,371,700 B2
(45) Date of Patent: Aug. 6, 2019

(54) IN-VITRO DIAGNOSTIC

(71) Applicant: Canon Medical Systems Corporation, Otawara-shi (JP)

(72) Inventors: Asuka Hirano, Nasushiobara (JP); Shoichi Kanayama, Otawara (JP); Ichiro Tono, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/611,077

(22) Filed: Jun. 1, 2017

(65) Prior Publication Data

US 2017/0350880 A1  Dec. 7, 2017

(30) Foreign Application Priority Data

Jun. 2, 2016 (JP) ................................. 2016-111222
May 19, 2017 (JP) ................................. 2017-099749

(51) Int. Cl.
G01N 21/75 (2006.01)
G01N 33/543 (2006.01)

(52) U.S. Cl.
CPC ... *G01N 33/54366* (2013.01); *G01N 2405/00* (2013.01)

(58) Field of Classification Search
CPC ......... G01N 33/5304; G01N 33/54366; G01N 2405/00
See application file for complete search history.

(56) References Cited

U.S. PATENT DOCUMENTS

| | | | |
|---|---|---|---|
| 6,222,619 B1 * | 4/2001 | Herron | G01N 33/54373 356/317 |
| 2009/0124024 A1 * | 5/2009 | Kasai | G01N 21/552 436/518 |
| 2013/0309779 A1 * | 11/2013 | Kasai | G01N 33/54373 436/501 |

FOREIGN PATENT DOCUMENTS

| | | |
|---|---|---|
| JP | 4505281 | 7/2010 |
| JP | 5322242 | 10/2013 |
| JP | 2013-238541 | 11/2013 |
| JP | 2014-66720 | 4/2014 |

* cited by examiner

*Primary Examiner* — Dennis White
(74) *Attorney, Agent, or Firm* — Oblon, McClelland, Maier & Neustadt, L.L.P.

(57) ABSTRACT

An in-vitro diagnostic includes a housing, a storage, and a blocking agent. The housing houses a liquid including a test substance included in a sample extracted from a subject. The storage stores a substance that specifically reacts with the test substance. The blocking agent is placed to separate the container and the storage.

5 Claims, 8 Drawing Sheets

IN-VITRO DIAGNOSTIC

CROSS-REFERENCE TO RELATED APPLICATIONS

This application is based upon and claims the benefit of priority from the prior Japanese Patent Application No. 2016-111222, filed Jun. 2, 2016 and No. 2017-99749, filed May 19, 2017, the entire contents of both which are incorporated herein by reference.

FIELD

Embodiments described herein relate generally to an in-vitro diagnostic.

BACKGROUND

For detection of protein from a sample using an immunological measurement method, it is known that an immune reaction between protein and antibodies or antigens is related to the tertiary structures of antibodies or antigens. It is also known that the protein detection accuracy decreases if the tertiary structures of antibodies or antigens vary. The in-vitro diagnostic used in this type of measurement usually is configured to immobilize a blocking agent such as bovine serum albumin (BSA) or polyethylene glycol (PEG) to a support to stabilize the tertiary structure of an antibody or an antigen bound with the support.

In addition, for detection of a particular signal in the measurement using the immunological measurement method, it is known that nonspecific coupling between protein in a sample and an antibody or an antigen, or a nonspecific signal caused by nonspecific adsorption of protein in a sample to a support adversely affects the detection of the particular signal. Accordingly, a blocking agent, etc. is added to a measurement solution in which a sample and a reagent component are mixed, in order to suppress occurrence of a nonspecific signal. In this case, the blocking agent may be a BSA, hydrolyzed vegetable protein, immune globulin, or casein. The blocking agent may be the same as or different from the aforementioned blocking agent used to stabilize the tertiary structure.

Even if a blocking agent to stabilize the tertiary structure of an antibody or an antigen is immobilized to a support of an in-vitro diagnostic, nonspecific binding of protein in a sample and an antibody or an antigen, or nonspecific adsorption of protein in a sample to a support cannot completely be prevented if a blocking agent is not added to the measurement solution. Thus, occurrence of a nonspecific signal cannot be sufficiently suppressed.

On the other hand, if a blocking agent is added to the measurement solution, the blocking agent has to be stirred throughout the measurement solution. Accordingly, even if there is dead volume, it is necessary to add a large amount of blocking agent in accordance with the volume of solution to be used, not the immune reaction amount. A blocking agent is generally mixed to a buffer solution prior to addition of the blocking agent to the measurement solution. However, since the blocking agent usually is protein or hydrolyzed protein, the blocking agent is difficult to be preserved stably in a liquid state. In addition, the measurement solution in which such a blocking agent is added has limitations for preserving conditions, for example, the solution can be preserved only for a short time at room temperature, or the solution needs to be preserved in a refrigerator. Furthermore, if the measurement solution into which such blocking agent is added is preserved in a refrigerator, the solution has to return to room temperature before measurement is carried out.

DETAILED DESCRIPTION

In general, according to one embodiment, an in-vitro diagnostic includes a housing, a storage, and a blocking agent. The housing houses a liquid including a test substance included in a sample extracted from a subject. The storage stores a substance that specifically reacts with the test substance. The blocking agent is placed to separate the container and the storage.

Hereinafter, embodiments will be described with reference to the accompanying drawings.

First Embodiment

Figure 1:
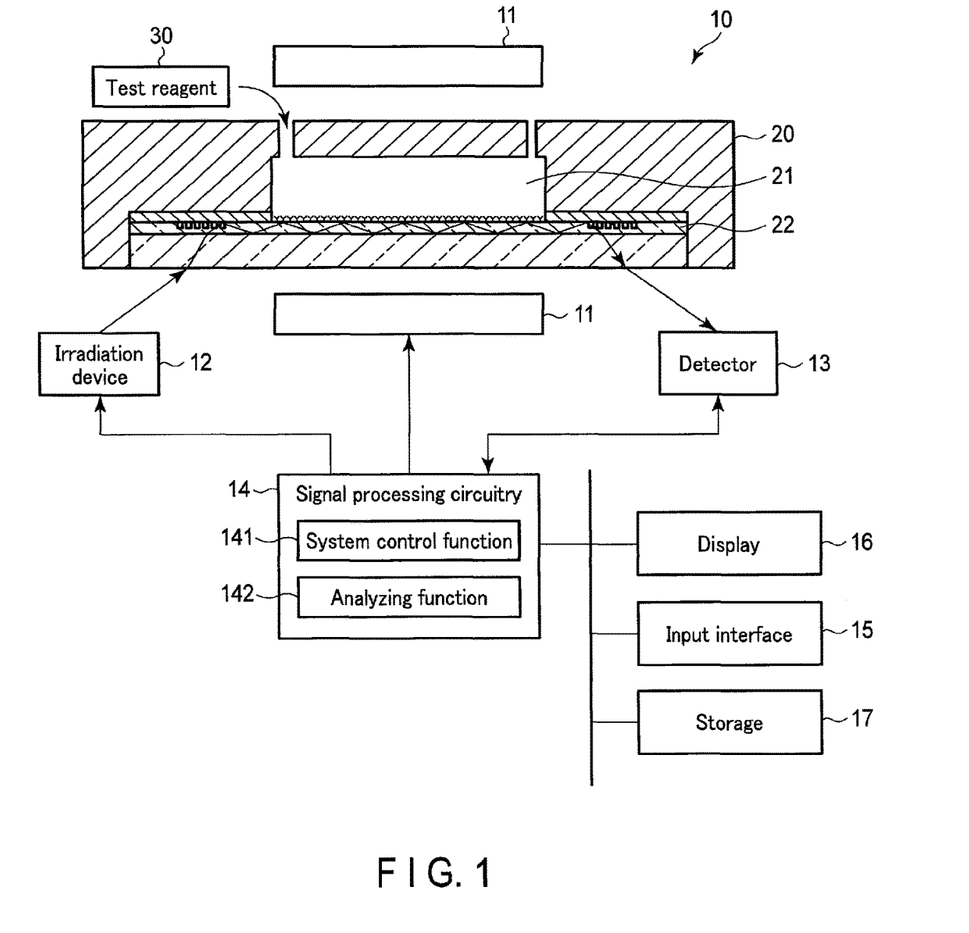
FIG. 1 is a diagram illustrating the configuration of a specimen measurement apparatus which uses an in-vitro diagnostic, according to the first embodiment.

FIG. 1 is a schematic diagram illustrating the configuration of a specimen measurement apparatus 10 which uses an in-vitro diagnostic, according to the first embodiment. The specimen measurement apparatus 10 shown in FIG. 1 is an apparatus that measures a test substance contained in a sample extracted from a subject, by using a sensing device 20 and a test reagent 30. In the first embodiment, the sensing device 20 corresponds to an in-vitro diagnostic.

The test reagent 30 is a diagnostic for generating a measurement solution to be housed in the sensing device 20. The test reagent 30 includes a reagent component that specifically reacts with a test substance, and an injection device. The reagent component is, for example, mixed with an aqueous solution such as a buffer solution and a sample extracted from a subject in the injection device. The measurement solution in which the reagent component, aqueous solution, and sample are mixed is housed in a reaction chamber 21 provided in the sensing device 20. The sensing device 20 includes an optical waveguide 22 provided to serve as a bottom surface of the reaction chamber 21.

The specimen measurement apparatus 10 shown in FIG. 1 includes magnetic field applying circuitry 11, an irradiation device 12, a detector 13, signal processing circuitry 14, an input interface 15, a display 16, and a storage 17.

The magnetic field applying circuitry 11 is provided with electromagnets that generate a magnetic field, the electromagnets being vertically separated by a predetermined distance. The magnetic field applying circuitry 11 applies downward and upward magnetic fields to the sensing device 20 when the sensing device 20 is placed between the electromagnets.

The irradiation device 12 irradiates the sensing device 20 with light such as a laser or an LED from the bottom. The detector 13 detects light emitted from the irradiation device 12 and propagated through the optical waveguide 22 provided in the sensing device 20.

The signal processing circuitry 14 is a processor that functions as a main unit of the specimen measurement apparatus 10. The signal processing circuitry 14 runs an operation program stored in the storage 17, etc., to implement a function corresponding to the program, namely, a system control function 141 and an analyzing function 142. The system control function 141 is a function of integrally controlling each element of the specimen measurement apparatus 10, based on input information input from the input interface 15. The analyzing function 142 is a function of calculating the amount of test substance included in a sample, based on light detected by the detector 13.

The input interface 15 is implemented, for example, by a mouse, keyboard, or a touch pad in which an instruction is input by contact to an operation surface. The input interface 15 receives various instructions from an operator. The input interface 15 is connected to the signal processing circuitry 14, for example, through a bus, and converts an operation instruction input by the operator into an electrical signal. The input interface 15 outputs the electrical signal to the signal processing circuitry 14. In the specification, the input interface 15 is not limited to a member that includes physical operation members such as a mouse and a keyboard, etc. For example, the input interface circuitry 15 may be electric signal processing circuitry that receives an electric signal corresponding to an operation instruction through an external input device independently provided from the specimen measurement apparatus 10, and outputs the electric signal to the signal processing circuitry 14.

The display 16 includes display interface circuitry and a display device, for example. For example, a CRT display, a liquid crystal display, an organic EL display, an LED display, a plasma display, or displays known in this technical field can be discretionarily applied as the display device. The display interface circuitry converts data indicating the calculation results into a video signal. The display device displays the video signal representing the calculation results.

Figure 2:
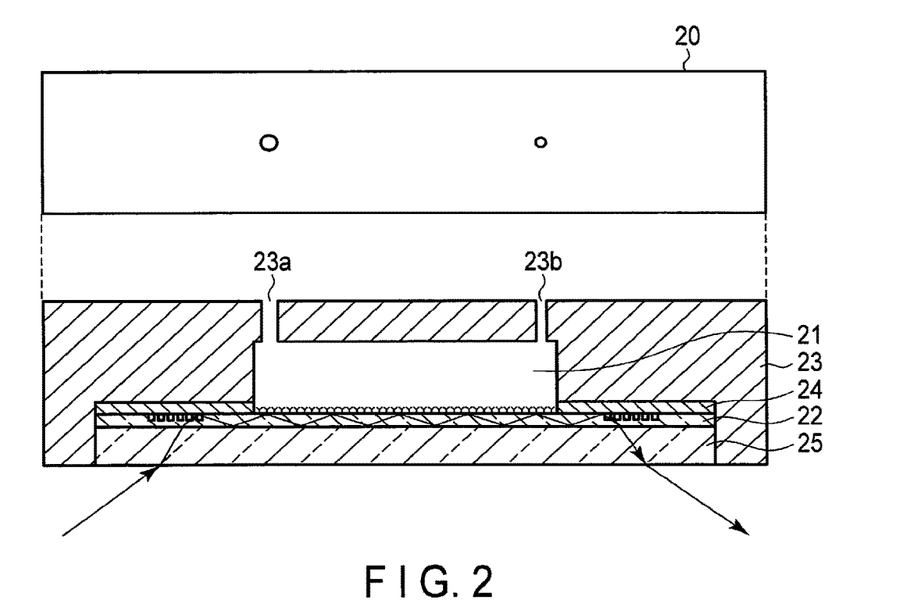
FIG. 2 is a diagram illustrating the configuration of a sensing device according to the first embodiment.

FIG. 2 is a schematic diagram illustrating an example configuration of the sensing device 20 according to the first embodiment. The sensing device 20 shown in FIG. 2 includes a plate-like optical waveguide 22, a cartridge frame 23, a plate-like shield membrane 24, and a plate-like transparent substrate 25. The sensing device 20 also includes a reaction chamber 21 that is defined by the optical waveguide 22, the cartridge frame 23, and the shield membrane 24, and houses the measurement solution.

The optical waveguide 22 is formed, for example, of an optically transparent material, a material acting as a substrate in which antigen-antibody reaction is performed, etc. An example of the optically transparent material is a glass, a resin, etc. An example of the material acting as a substrate for antigen-antibody reaction is a membrane such as a nitrocellulose membrane, etc. The optical waveguide 22 serves as an optical path of light that enters from the transparent substrate 25 and exits to the transparent substrate 25. That is, the optical waveguide 22 has a function similar to a core (core material) in an optical fiber. The shield membrane 24 and the transparent substrate 25 are formed of a material having a different refractive index from the optical waveguide 22. The shield membrane 24 and the transparent substrate 25 function as a cladding that reflects light completely on a boundary surface with respect to the optical waveguide 22, and confines light in the optical waveguide 22. The shield membrane 24 and the transparent substrate 25 also physically protect the optical waveguide 22.

Figure 3:
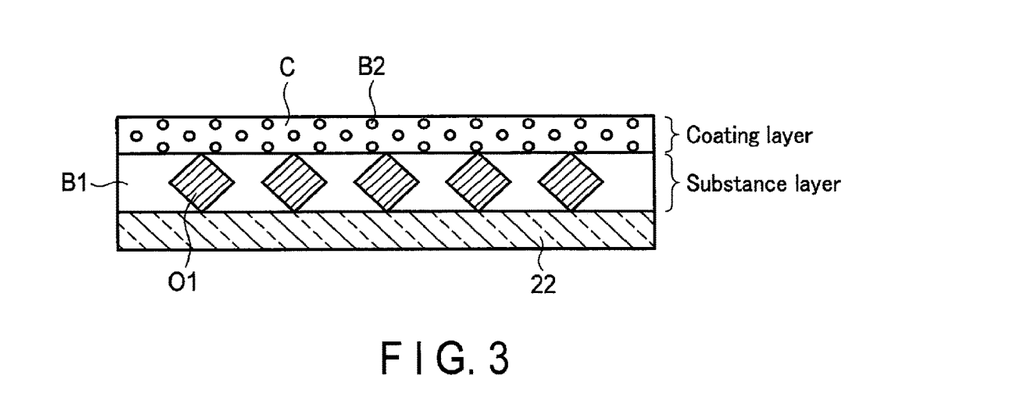
FIG. 3 is a diagram illustrating the surface structure of an optical waveguide depicted in FIG. 2.

The optical waveguide 22 functions as a support that is bound with a substance which specifically reacts with a test substance included in a sample extracted from a subject, on the upper side surface. FIG. 3 is a schematic diagram illustrating the enlarged upper side surface of the optical waveguide 22 depicted in FIG. 2. A substance layer is formed on the surface of the optical waveguide 22. In the present embodiment, a layer formed on the surface of the optical waveguide 22 and formed of a substance O1 that specifically reacts with a test substance and a blocking agent B1 is called a "substance layer". The substance layer can be called a storage that stores a substance that specifically reacts with a test substance. In addition, in the present embodiment, the substance O1 represents an antigen when the test substance serves as an antibody, and represents an antibody when the test substance serves as an antigen. The substance O1 may represent a peptide. The substance O1 is bound to the surface of the optical waveguide 22.

The blocking agent B1 is immobilized on part of the surface of the optical waveguide 22 where the substance O1 is not bound. The blocking agent B1 is, for example, BSA, PEG, and a PEG formulation, etc., and may be used solely or in combination. The blocking agent B1 has a function of stabilizing the tertiary structure of the substance O1. The blocking agent B1 also has a function of preventing a test substance from being non-specifically adsorbed to the optical waveguide 22 where the substance O1 is bound, and also of preventing accurate measurement of the test substance from becoming unable to be conducted.

In FIG. 3, a coating layer is formed on the surface of the substance layer. In FIG. 3, the substance layer is depicted as thicker than the coating layer. However, the coating layer becomes overwhelmingly thicker than the substance layer in the actual situation. The coating layer is a dry film formed by drying a coating agent C for stable preservation. It is preferable that the coating agent C is saccharide such as sucrose, maltose, trehalose, pullulan, hydroxypropylcellulose (HPC), or dextran, etc. The coating layer includes a blocking agent B2. The blocking agent B2 has a function of preventing a test substance from being non-specifically bound with the substance O1 bound to the optical waveguide 22, and also of preventing accurate measurement of the test substance from becoming unable to be conducted. The blocking agent B2 is, for example, BSA, casein, sericin, blocking peptide fragment (BPF), or fish collagen peptide (FCP), etc., and is preferably an agent that affects a sample in the measurement solution. The blocking agent B2 is discretionarily selected in accordance with measurement items.

The cartridge frame 23 is a case of the sensing device 20. A first concave portion is formed on the lower surface of the cartridge frame 23. A second concave portion that forms the upper and side surfaces of the reaction chamber 21 is formed in part of the upper surface of the first concave portion. In the first concave portion, the shield membrane 24, the optical waveguide 22, and the transparent substrate 25 are arranged in the order given from the top. A hole 23a is formed close to one end of the upper surface of the second concave portion so as to extend upward through the cartridge frame 23, and a hole 23b is formed close to the other end so as to extend upward through the cartridge frame 23.

The shield membrane 24 has an opening at the position of the second concave portion of the cartridge frame 23. The shield membrane 24 is arranged with the upper surface in contact with the upper surface of the first concave portion of the cartridge frame 23 and the lower surface in contact with the upper surface of the optical waveguide 22.

The transparent substrate 25 is made of a material that passes light emitted from the irradiation device 12. The transparent substrate 25 is arranged with the upper surface in contact with the lower surface of the optical waveguide 22.

The reaction chamber 21 is a housing that houses the measurement solution. The reaction chamber 21 is arranged with the upper surface defined by the upper surface of the second concave portion of the cartridge frame 23. The reaction chamber 21 is arranged with the side surfaces defined by the side surfaces of the second concave portion of the cartridge frame 23 and the opened surface of the shield membrane 24. The reaction chamber 21 is arranged with the lower surface defined by the upper surface of the optical waveguide 22. The reaction chamber 21 is arranged with the lower surface on which the substance layer and the coating layer as shown in FIG. 3 are fixed.

Next, an example of the procedure of forming the substance layer and the coating layer on the surface of the optical waveguide 22 is explained.

First, a predetermined amount of blocking agent B2 is put into the coating agent C to prepare the coating agent C that includes the blocking agent B2. Otherwise, a chemically-modified support (optical waveguide 22) is prepared. Then, after the prepared support is activated by an activator, etc., a substance O1 is spotted to the activated support, and the substance O1 is bound with the support. The blocking agent B1 is allowed to affect an unreacted active group in the support to store and stabilize the tertiary structure of the substance O1 bound with the support. By the above procedure, the substance layer is formed on the surface of the support.

Next, a predetermined amount of the coating agent C including the blocking agent B2 is applied on the surface of the substance layer. The amount of the coating agent C including the blocking agent B2 to be applied varies depending on the measurement items, but the same amount of the coating agent C is applied for the same measurement item. Moisture of the applied coating agent C is evaporated by any of decompression drying, freeze drying, air drying, and nitrogen drying, to dry the support. By this process, the coating layer including the blocking agent B2 is formed on the surface of the substance layer. After the substance O1 is bound with the support, the process of washing the surface of the support by the buffer solution such as PBS or purified water may be adopted before applying the coating agent C.

By the above process, the optical waveguide 22 is prepared in which the substance layer is formed on the surface thereof, and the coating layer including the blocking agent B2 is formed on the surface of the substance layer.

Next, an operation example of the specimen measurement apparatus 10 that uses the sensing device 20 according to the first embodiment is explained. In the following example, a reagent component 31 contained in a test reagent 30 includes a first antibody that is bound with the test substance A serving as an antigen, and a fine particle in which the first antibody is immobilized. The substance O1 bound to the surface of the optical waveguide 22 of the sensing device 20 is a second antibody that is bound with the test substance A serving as an antigen.

Figure 4:
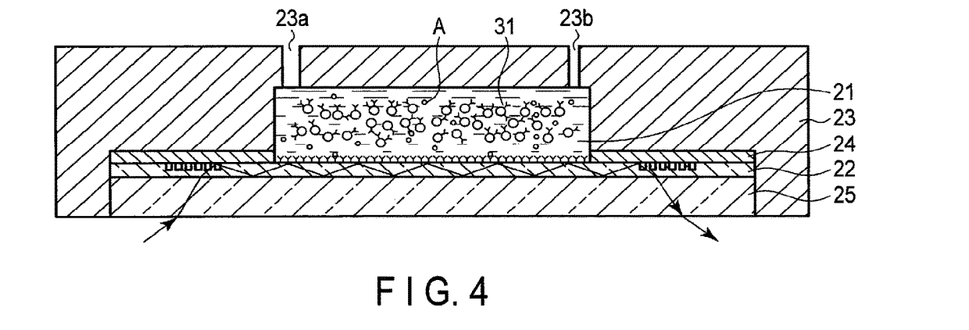
FIG. 4 is a diagram illustrating a sensing device when a measurement solution is housed in a reaction chamber depicted in FIG. 2.

First, an aqueous solution such as a buffer solution, the reagent component 31, and a sample extracted from a subject are mixed in the injection device of the test reagent 30. The measurement solution in which the aqueous solution, the reagent component 31, and the sample are mixed flows into the reaction chamber 21 of the sensing device 20 from the injection device through the hole 23a of the cartridge frame 23. At this time, air in the reaction chamber 21 is discharged from the hole 23b of the cartridge frame 23. FIG. 4 is a schematic diagram showing the reaction chamber 21 when the measurement solution is housed therein. In the first embodiment, the reaction chamber 21 is explained as an example of a reaction space. However, the reaction space may be a tube space formed by a device having a flow path. It is preferable that agitation does not occur in the reaction space during reaction.

Figure 5:
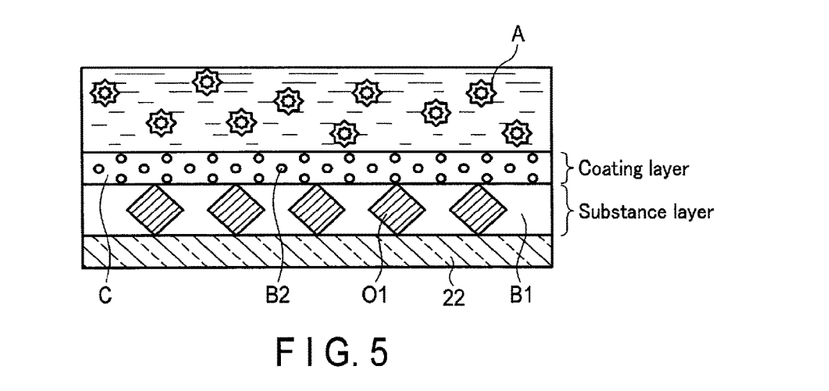
FIG. 5 is a diagram illustrating the surface structure of an optical waveguide when in contact with the measurement solution.
Figure 6:
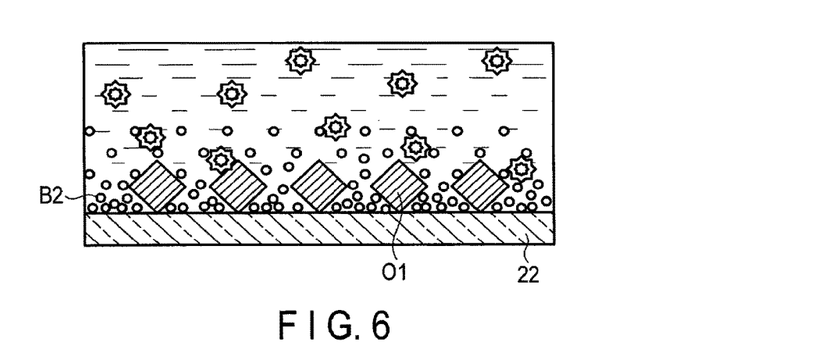
FIG. 6 is a diagram illustrating the surface structure of an optical waveguide when a coating layer depicted in FIG. 5 is dissolved in the measurement solution.

If the measurement solution is in contact with the coating layer on the optical waveguide 22 under the reaction chamber 21, as shown in FIG. 5, the coating layer including the blocking agent B2 is dissolved rapidly. By the dissolution of the coating layer, the blocking agent B2 is also dissolved. The dissolved blocking agent B2 spreads on the surface of the optical waveguide 22. By this process, as shown in FIG. 6, the blocking agent B2 is distributed with a concentration that becomes lower away from the surface of the optical waveguide 22. Accordingly, the test substance A close to the optical waveguide 22 is exposed to the blocking agent B2 distributed with the high concentration. As a result, nonspecific binding of the test substance A and the second antibody bound to the optical waveguide 22 and nonspecific adsorption of the test substance A to the optical waveguide 22 are suppressed.

If the reaction chamber 21 is filled with the measurement solution, light is emitted from the irradiation device 12. The emitted light penetrates the transparent substrate 25 of the sensing device 20 and enters the optical waveguide 22 from one end side. The light that has entered is deflected and then propagated through the optical waveguide 22 toward the other end. The light is propagated through the region of the optical waveguide 22 under the reaction chamber 21 and exits from the other end side of the optical waveguide 22 after being deflected to an angle at which the light is able to exit from the optical waveguide 22. The detector 13 detects the light that has exited from the optical waveguide 22 and passed through the transparent substrate 25.

The magnetic field applying circuitry 11 applies a downward magnetic field to the reaction chamber 21 and then applies an upward magnetic field to the reaction chamber 21. The reagent component 31 in the measurement solution housed in the reaction chamber 21 is bound with the first antibody immobilized on a magnetic particle, thereby trapping the test substance A. When the downward magnetic field is applied, the test substance A trapped by the reagent component 31 is bound with the second antibody immobilized on the lower surface of the reaction chamber 21. Then, when the upward magnetic field is applied, only the reagent component 31 that does not trap the test substance A by the second antibody moves upward.

When the test substance A trapped by the reagent component 31 is bound with the second antibody immobilized on the lower surface of the reaction chamber 21, the intensity of the light propagating through the optical waveguide 22 decreases due to scattering and absorption of the light in the region under the reaction chamber 21. The intensity of the light that exits from the optical waveguide 22 changes depending on the amount of the test substance A bound with the second antibodies immobilized on the lower surface of the reaction chamber 21. When the upward magnetic field is being applied, the signal processing circuitry 14 calculates the amount of the test substance A in the measurement solution based on the intensity of the light that exits from the optical waveguide 22. The display 16 displays the amount of the test substance A calculated by the signal processing circuitry 14.

As stated above, the sensing device 20 according to the first embodiment includes the support, the substance layer in which a substance that specifically reacts with a test substance is bound with the surface of the support, and the dry film that includes a soluble coating agent and a blocking agent and covers the surface of the substance layer. That is, the substance layer is formed by binding the substance O1 with the optical waveguide 22, and immobilizing the blocking agent B1 to the optical waveguide 22. The soluble coating agent C including the blocking agent B2 is applied on the surface of the substance layer, and the optical waveguide 22 coated by the coating agent C is dried. By the above process, a soluble dry film including the blocking agent B2 is formed on the surface of the substance layer in the optical waveguide 22.

When the measurement solution is in contact with the optical waveguide 22, the blocking agent B2 is dissolved rapidly. Then, the test substance close to the optical waveguide 22 is exposed to the highly concentrated blocking agent B2. As a result, nonspecific binding of the test substance and the substance O1 bound to the optical waveguide 22 and nonspecific adsorption of the test substance to the optical waveguide 22 can be suppressed.

Therefore, the in-vitro diagnostic according to the first embodiment realizes easy preservation and high blocking effects with a small amount of a medicinal agent. In addition, part of a liquid reagent having poor stability is dried and preserved in the sensing device 20, thereby simplifying the component of the test reagent 30. Accordingly, the preservation stability of the entire test kit including the test reagent 30 and the sensing device 20 can be improved.

(Modification)

Figure 7:
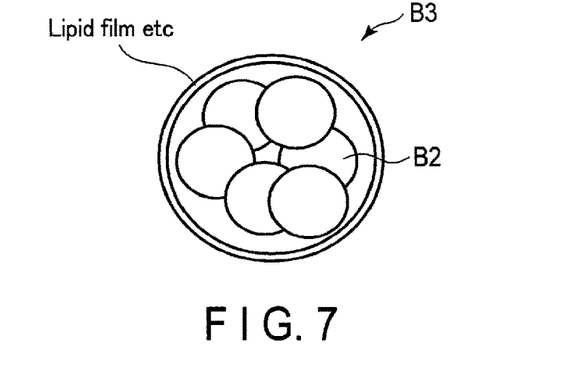
FIG. 7 is a diagram illustrating the structure of a blocking agent according to a modification of the first embodiment.

In the first embodiment, the coating agent C including the blocking agent B2 is applied on the surface of the substance layer formed in the optical waveguide 22, and the optical waveguide 22 coated by the coating agent C is dried. However, the embodiments are not limited thereto. A coating agent C that includes a blocking agent B3 generated by covering a blocking agent B2 with a lipid film, etc. is applied on the surface of a substance layer formed on an optical waveguide 22. The optical waveguide 22 coated by the coating agent C may be dried. FIG. 7 is a schematic diagram of the structure of the blocking agent B3 according to the modification. The lipid film shown in FIG. 7 is, for example, a liposome of a lipid bimolecular membrane, which has a capsular structure. The lipid film includes, for example, a liquid blocking agent B2 inside thereof.

Figure 8:
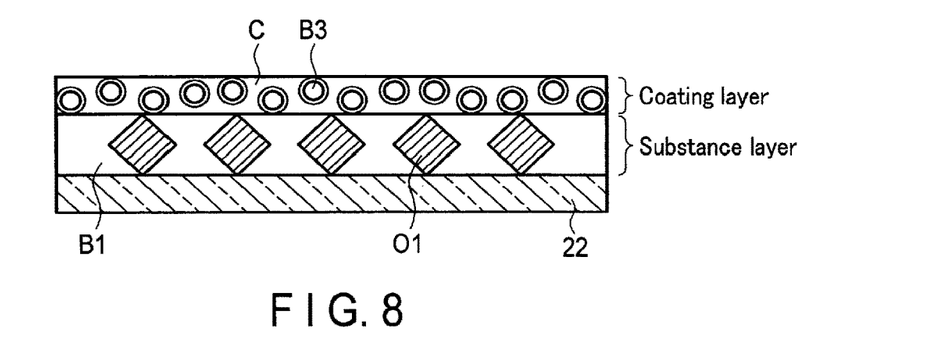
FIG. 8 is a diagram illustrating the surface structure of an optical waveguide when a blocking agent depicted in FIG. 7 and a coating layer are applied on a surface of a substance layer.
Figure 9:
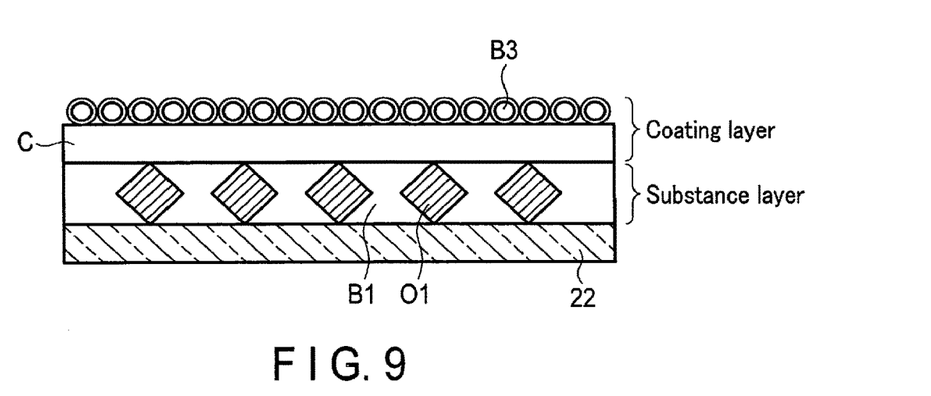
FIG. 9 is a diagram illustrating another example of the surface structure of an optical waveguide when a blocking agent depicted in FIG. 7 and a coating layer are applied on the surface of the substance layer.

FIG. 8 and FIG. 9 are schematic diagrams of the enlarged upper surface of the optical waveguide 22 in which the blocking agent B3 and the coating agent C are applied on the surface of the substance layer. In FIG. 8, the blocking agent B3 dispersed in the coating agent C is applied to the optical waveguide 22. In FIG. 9, the blocking agent B3 is applied on the surface of the coating agent C.

Next, an example of the procedure of forming the substance layer and the coating layer on the surface of the optical waveguide 22 is explained. An example of the procedure of forming the substance layer and the coating layer on the surface of the optical waveguide 22, as shown in FIG. 8, is explained below.

First, a blocking agent B3 is prepared by dissolving phospholipid such as lecithin in the liquid blocking agent B2. The prepared blocking agent B3 is put into a coating agent C to prepare the coating agent C that includes the blocking agent B3. In addition, a chemically-modified support (optical waveguide 22) is prepared.

A substance layer is formed on the surface of the prepared support. A predetermined amount of the coating agent C including the blocking agent B3 is applied to the surface of the substance layer. Moisture of the applied coating agent C is evaporated by a predetermined drying method to dry the support. By this process, the coating layer including the blocking agent B3 is formed on the surface of the substance layer.

Next, an example of the procedure of forming the substance layer and the coating layer on the surface of the optical waveguide 22, as shown in FIG. 9, is explained below.

First, a blocking agent B3 is prepared by dissolving phospholipid such as lecithin in the liquid blocking agent B2. In addition, a chemically-modified support (optical waveguide 22) is prepared.

A substance layer is formed on the surface of the prepared support. The coating agent C is applied to the surface of the substance layer. Moisture of the applied coating agent C is evaporated by a predetermined drying method. Then, liquid including the blocking agent B3 is applied on the surface of the coating agent C that has been dried. Moisture of the applied liquid including the blocking agent B3 is evaporated by a predetermined drying method such as freeze drying, to dry the support. By this process, the coating layer including the blocking agent B3 is formed on the surface of the substance layer. The prepared blocking agent B3 may be put into a buffer solution, etc., and the buffer solution, etc. including the blocking agent B3 may be applied to the surface of the coating agent C that has been dried.

Next, an example of the procedure in which the blocking agent B3 is dissolved in the optical waveguide 22 according to the modification is explained below. In the following example, it is assumed that surfactant is included in a buffer solution of a test reagent 30.

First, an aqueous solution such as a buffer solution, a reagent component 31, and a sample extracted from a subject are mixed in an injection device to generate a test reagent 30. The measurement solution in which the aqueous solution, the reagent component 31, and the sample are mixed flows into the reaction chamber 21 of the sensing device 20 from the injection device. The measurement solution that has entered the reaction chamber 21 is brought into contact with the coating layer as shown in FIG. 8 or FIG. 9.

Figure 10:
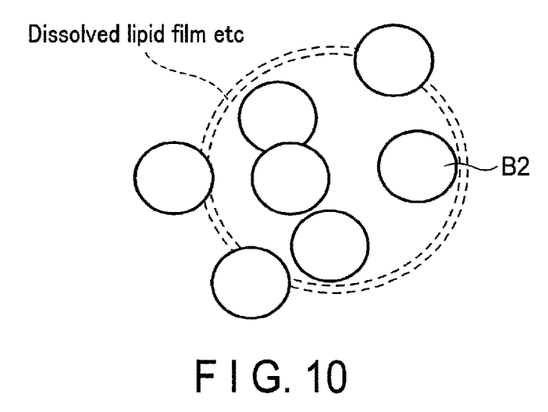
FIG. 10 is a diagram illustrating a blocking agent when a lipid film depicted in FIG. 7 is dissolved.

When the measurement solution is in contact with the coating layer, a coating agent C is dissolved rapidly. As shown in FIG. 10, a lipid film of a blocking agent B3 is dissolved by the surfactant included in the measurement solution. Then, a blocking agent B2 covered by the lipid film is dissolved. By this process, the blocking agent B2 is distributed with a concentration that becomes lower away from the surface of the optical waveguide 22. Accordingly, a test substance close to the optical waveguide 22 is exposed to the blocking agent B2 distributed with the high concentration. As a result, nonspecific binding of the test substance and a substance O1 bound to the optical waveguide 22 and nonspecific adsorption of the test substance to the optical waveguide 22 are suppressed.

As stated above, in the modification of the first embodiment, a blocking agent B3 is prepared by covering a blocking agent B2 by a lipid film. The prepared blocking agent B3 is applied on the substance layer formed on the surface of the optical waveguide 22, and the support is dried. By this processing, it is possible to prevent the blocking agent B2 covered by the lipid film of the blocking agent B3 from being dried when the optical waveguide 22 is dried.

Accordingly, it is possible to prepare the in-vitro diagnostic in which the blocking agent B2 exerts its effects in the liquid state that can be easily preserved, and is expected to realize high blocking effect with a small amount of a medicinal agent.

Second Embodiment

In the second embodiment, a test reagent 30, which is shown in FIG. 1, is a diagnostic for generating a measurement solution to be housed in a sensing device 20 that corresponds to an in-vitro diagnostic.

Figure 11:
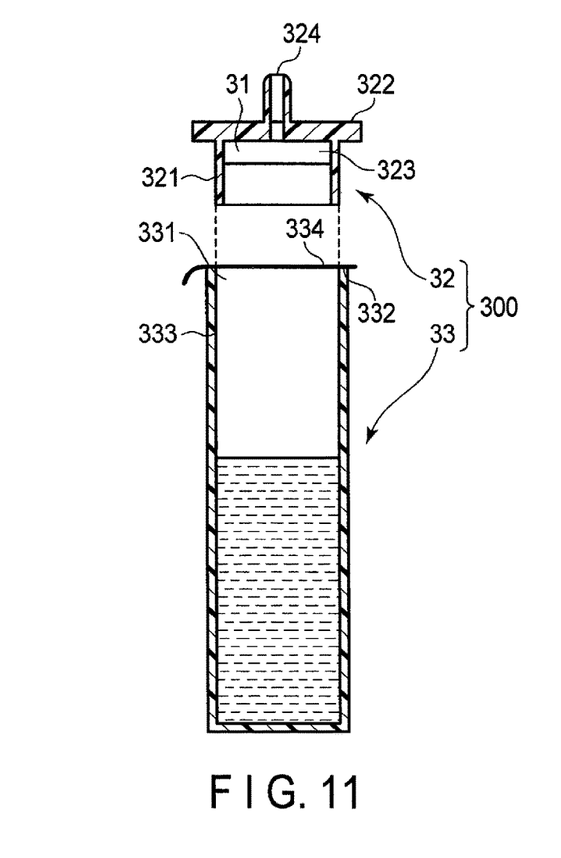
FIG. 11 is a cross-sectional view of the structure of a test reagent according to the second embodiment.

FIG. 11 is a cross-sectional view of the structure of a test reagent 30 according to the second embodiment. The test reagent 30 shown in FIG. 11 includes a reagent component 31 and an injection device 300 that stores the reagent component 31. The injection device 300 includes an injection tool 32 and a container 33.

The injection tool 32 includes a fitting part 321, a collar 322, and a discharge opening 324. The fitting part 321 is formed in the manner that an outer diameter is essentially the same as an inner diameter of the container 33. The fitting part 321 is fit into an inner surface 333 of the container 33 when inserting the injection tool 32 to the container 33.

The collar 322 is formed in the manner that an outer diameter is greater than an outer diameter of the container 33. When inserting the injection tool 32 to the container 33, the lower surface of the collar 322 is brought into contact with the upper surface 332 of the container 33. The injection tool 32 is fit into the container 33 by means of the fitting part 321 and the collar 322, and seals the container 33 as a lid.

A reagent holding portion 323 is loaded inside of the fitting part 321 by being in contact with an inner surface of the fitting part 321. Specifically, the reagent holding portion 323 is, for example, a columnar shape, and an outside diameter of the reagent holding portion 323 is formed greater than an inside diameter of the fitting part 321. The reagent holding portion 323 is brought into contact with an inner surface of the fitting part 321 by press-fitting into the fitting part 321. The reagent holding portion 323 is a porous sheet formed of a resin such as polyethylene, etc.

The discharge opening 324 is a nozzle from which liquid is discharged. The discharge opening 324 is an opening through a measurement solution is allowed to flow from a hole 23a of the sensing device 20. The injection tool 32 may be loaded to a filter that is in contact with the inner surface of the fitting part 321. In this case, the reagent holding portion 323 is provided between the filter and the discharge opening 324.

The container 33 is formed, for example, of resin or low density polyethylene, etc., and has flexibility and permeability. The container 33 has an opening 331 at one end in a longitudinal direction, and has a closed-end. The container 33 houses a predetermined amount of an aqueous solution such as a buffer solution, etc. The container 33 has a structure that the opening 331 is sealed by a removable sealing member 334 so as to prevent an aqueous solution from leaking to the outside. The container 33 functions as a housing in which a sample extracted from a subject is supplied, and a solution mixture in which the sample is mixed with the aqueous solution is housed.

Figure 12:
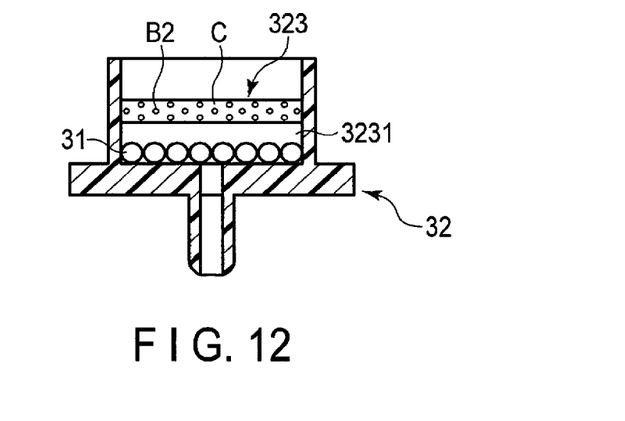
FIG. 12 is a diagram illustrating the structure of a reagent holding portion depicted in FIG. 11.
Figure 13:
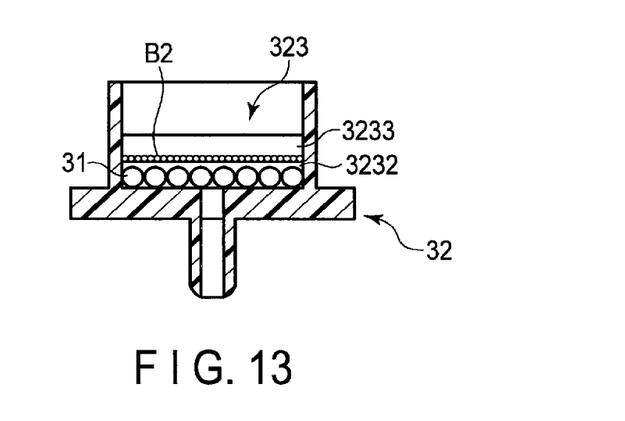
FIG. 13 is a diagram illustrating another example of the structure of the reagent holding portion depicted in FIG. 11.

The reagent holding portion 323 stores the reagent component 31 that specifically reacts with a test substance and a blocking agent B2. FIG. 12 and FIG. 13 are schematic diagrams showing an example configuration of a reagent holding portion 323 depicted in FIG. 11. The reagent holding portion 323 shown in FIG. 12 has a first sheet 3231.

The first sheet 3231 stores the reagent component 31 that specifically reacts with a test substance inside of a hole. That is, the first sheet 3231 is a storage that stores a substance that specifically reacts with a test substance. The reagent component 31 is formed from a substance that specifically reacts with a test substance and a fine particle to which the substance is immobilized. In the present embodiment, a substance included in the reagent component 31 represents an antigen when the test substance serves as an antibody, and represents an antibody when the test substance serves as an antigen. The substance included in the reagent component 31 may represent peptide.

A coating layer is formed on the surface of the first sheet 3231 close to the opening. The coating layer is a dry film formed by drying a coating agent C for stable preservation. The coating agent C preferably is saccharide such as sucrose, maltose, trehalose, pullulan, HPC, and dextran, etc.

The coating layer includes a blocking agent B2. The blocking agent B2 has a function of preventing a test substance from being nonspecifically bound with the fine particles on which the substance is immobilized, and also preventing disablement of accurate measurement of the test substance. The blocking agent B2 is, for example, BSA, casein, sericin, BPF, and FCP, etc., and is preferably an agent that affects a sample in the measurement solution. The blocking agent B2 is discretionarily selected in accordance with measurement items. In the second embodiment, the blocking agent B2 included in the coating layer may have the same component as in the blocking agent B2 included in the coating layer in the first embodiment or have the different component.

The reagent holding portion 323 shown in FIG. 13 has a second sheet 3232 and a third sheet 3233.

The second sheet 3232 stores the reagent component 31 that specifically reacts with a test substance inside of a hole. That is, the second sheet 3232 is a storage that stores a substance that specifically reacts with a test substance. The third sheet 3233 is formed on the surface of the second sheet 3232 close to the opening. The third sheet 3233 stores the blocking agent B2 inside of a hole. The stacking order of the second sheet 3232 and third sheet 3233 may be reversed.

Next, an example of the procedure of preparing the reagent holding portion 323 loaded in the injection tool 32 is explained. An example of the procedure of preparing the reagent holding portion 323 as shown in FIG. 12 is explained.

First, a liquid reagent in which the reagent component 31 whose dry weight is n times (n is a positive number greater than 1.0) a predetermined weight is dissolved is prepared. A predetermined amount of blocking agent B2 is put into a coating agent C to prepare the coating agent C that includes the blocking agent B2. In addition, a sheet-like member that is made of polyethylene, and an area of which is n times an inner cross-sectional area of the fitting part 321 of the injection tool 32 is prepared. When the reagent holding portion 323 is inserted in the fitting part 321 by press fitting, the area of the sheet-like member is n times or more than the inner cross-sectional area of the fitting part 321. A container with a flat bottom surface is prepared as well.

After the container is arranged so that the surface of the prepared member becomes level, the liquid reagent is applied or sprayed so as to form an even layer on the surface of the member. After moisture of the liquid reagent that has been applied or sprayed is evaporated, the member is turned over, and a predetermined amount of the coating agent C including the blocking agent B2 is applied to the reverse surface of the member. After moisture of the applied coating agent C is evaporated to dry by any of decompression drying, freeze drying, air drying, and nitrogen drying, the member is cut into a predetermined size to prepare the first sheet 3231. By the above process, the reagent holding portion 323 is prepared.

Next, an example of the procedure of preparing the reagent holding portion 323 loaded to the injection tool 13 as shown in FIG. 12 is explained.

First, a liquid reagent is prepared in which the reagent component 31, whose dry weight is n times (n is a positive number greater than 1.0) a predetermined weight, is dissolved. A predetermined amount of liquid blocking agent B2 is prepared. In addition, a first sheet-like member and a second sheet-like member that are made of polyethylene are prepared, and an area of which is n times the inner cross-sectional area of the fitting part 321 of the injection tool 32. When the reagent holding portion 323 is inserted in the fitting part 321 by press-fitting, the area of the first and second sheet-like members is n times or more than the inner cross-sectional area of the fitting part 321. A container with a flat bottom surface is prepared as well.

After the container is arranged so that the surface of the prepared first member becomes level, the liquid reagent is applied or sprayed so as to form an even layer on the surface of the first member. After moisture of the applied or sprayed liquid reagent is evaporated to dry, the first member is cut into a predetermined size to prepare the second sheet 3232.

After the container is arranged so that the surface of the prepared second member becomes level, the liquid blocking agent B2 is applied or sprayed so as to form an even layer on the surface of the second member. After moisture of the applied or sprayed liquid blocking agent B2 is evaporated to dry, the second member is cut into a predetermined size to prepare the third sheet 3233. The prepared third sheet 3233 is stacked onto the prepared second sheet 3232. By the above process, the reagent holding portion 323 is prepared.

Next, an example of the procedure of housing the measurement solution in a reaction chamber 21 of a sensing device 20 from an injection device 300 will be explained. In the following example, a reagent component 31 contained in a test reagent 30 includes a first antibody that is bound with a test substance A serving as an antigen, and a fine particle to which the first antibody is immobilized.

Figure 14:
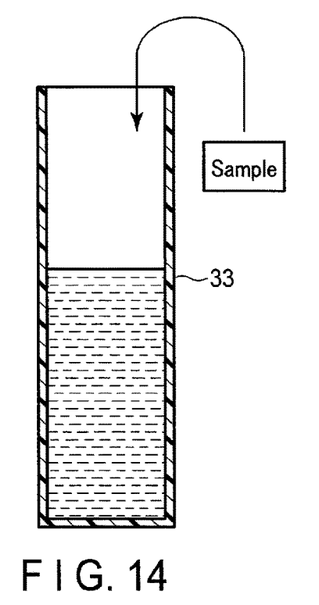
FIG. 14 is a diagram explaining the procedure for using the test reagent depicted in FIG. 11.

A user such as a doctor peals a sealing member 334 off from the container 33 of the injection device 300. Next, as shown in FIG. 14, the user puts a sample extracted from a subject into an aqueous solution within the container 33. After putting the sample in, the user inserts the injection tool 32 into the opening 331 of the container 33. By this process, the container 33 is sealed.

Figure 15:
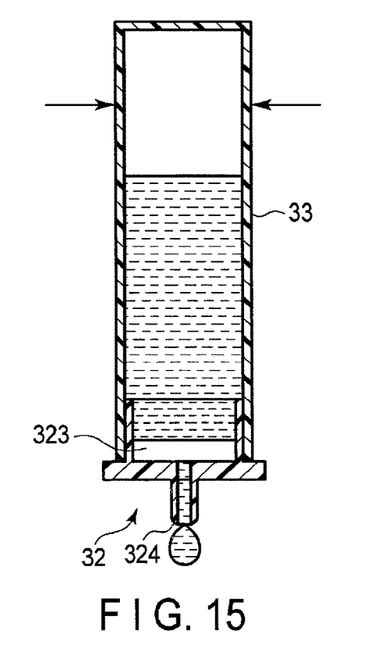
FIG. 15 is a diagram explaining the procedure for using the test reagent depicted in FIG. 11.

Next, the user upends the injection device 300 so that the injection tool 32 faces down, as shown in FIG. 15. Then, the solution mixture in which the aqueous solution and the sample are mixed is brought into contact with the reagent holding portion 323. At the reagent holding portion 323, the solution mixture is brought into contact with the blocking agent B2, and the blocking agent B2 is then dissolved in the solution mixture. Next, the solution mixture in which the blocking agent B2 is dissolved is brought into contact with the reagent component 31, and the reagent component 31 is dissolved in the solution mixture. By this process, the solution mixture including the blocking agent B2 in high concentration is brought into contact with the reagent component 31. Accordingly, the reagent component 31 is exposed to the blocking agent B2 distributed with the high concentration. As a result, nonspecific binding of a test substance A to a magnetic particle in which the first antibody is immobilized is suppressed.

Next, the user inserts the discharge opening 324 of the injection tool 32 into a hole 23a of the cartridge frame 23 of the sensing device 20. The user holds and presses the container 33 in the directions indicated by arrows shown in FIG. 15. By the pressure, the measurement solution in which the blocking agent B2 and the reagent component 31 are dissolved in the solution mixture is instilled from the discharge opening 324. The measurement solution instilled from the discharge opening 324 flows into the reaction chamber 21 of the sensing device 20.

As stated above, the test reagent 30 according to the second embodiment includes a container that houses a predetermined aqueous solution, a holding portion that stores a substance that specifically reacts with a test substance and a blocking agent, and an injection tool to which the holding portion is loaded, and a discharge opening from which liquid that has contacted the holding portion is discharged. That is, the reagent holding portion 323 that stores the dried blocking agent B2 and reagent component 31 is loaded to the injection tool 32 of the test reagent 30. With this configuration, the dried blocking agent B2 is arranged close to the reagent component 31.

In addition, when liquid is in contact with the reagent holding portion 323, the blocking agent B2 is dissolved rapidly, and the liquid including the blocking agent B2 in the high concentration is brought into contact with the reagent component 31. As a result, nonspecific binding of a test substance to a fine particle, in which a substance that specifically reacts with the test substance is immobilized, can be effectively suppressed.

Therefore, the in-vitro diagnostic according to the second embodiment realizes easy preservation and high blocking effects with a small amount of a medicinal agent. In addition, since part of a liquid reagent having poor stability is dried and stored in the injection tool 32 of the test reagent 30, the preservation stability of the entire test kit including the injection device and the sensing device 20 can be improved.

(Modification)

In the second embodiment, the example in which the reagent holding portion 323 stores the dried blocking agent B2 was explained. However, the embodiments are not limited thereto. A blocking agent B3 in which a blocking agent B2 is covered with a lipid film, etc. may be prepared, and the reagent holding portion 323 may store the blocking agent B3. The structure of the blocking agent B3 is the same as that shown in FIG. 7, FIG. 16 to FIG. 18 are schematic diagrams showing an example structure of a reagent holding portion 323 depicted in FIG. 11.

Figure 16:
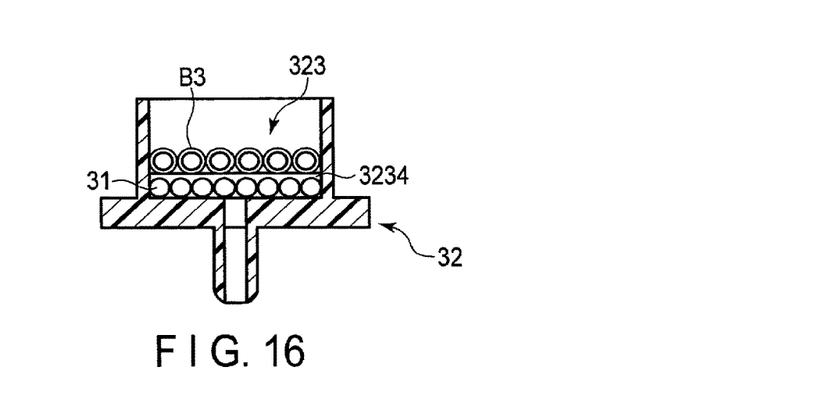
FIG. 16 is a diagram illustrating the structure of a reagent holding portion according to a modification of the second embodiment.

The reagent holding portion 323 shown in FIG. 16 has a fourth sheet 3234. The fourth sheet 3234 stores a reagent component 31 that specifically reacts with a test substance inside of a hole. That is, the fourth sheet 3234 is a storage that stores a substance that specifically reacts with a test substance. A blocking agent B3 covers a surface of the fourth sheet 3234 close to the opening.

Figure 17:
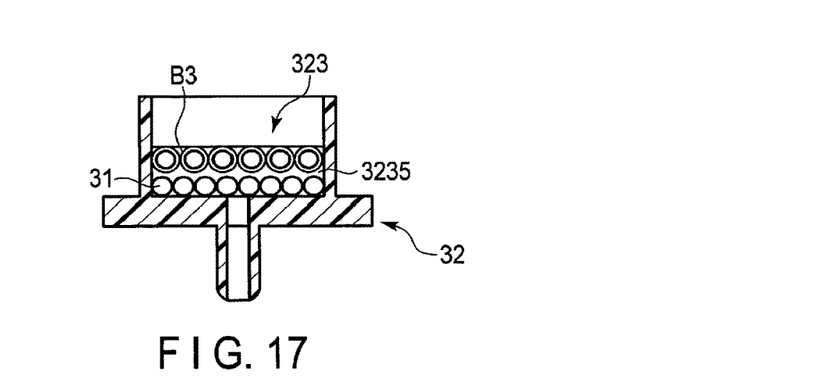
FIG. 17 is a diagram illustrating another example of the structure of a reagent holding portion according to a modification of the second embodiment.

The reagent holding portion 323 shown in FIG. 17 has a fifth sheet 3235. The fifth sheet 3235 stores the reagent component 31 and the blocking agent B3 inside of a hole. That is, the fifth sheet 3235 is a storage that stores a substance that specifically reacts with a test substance.

Figure 18:
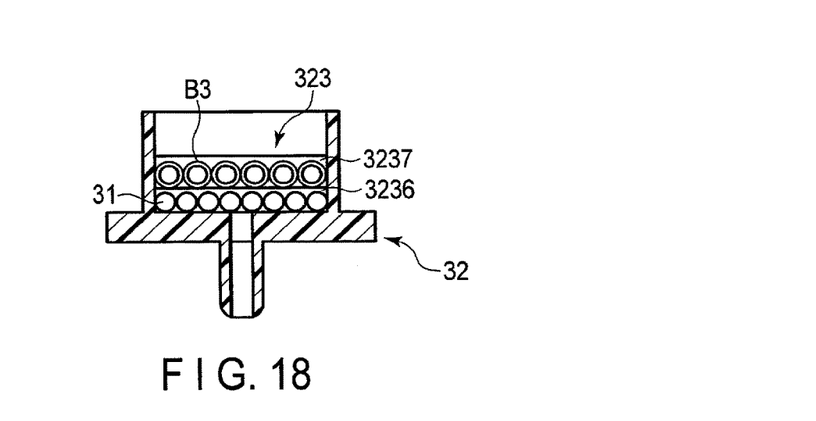
FIG. 18 is a diagram illustrating another example of the structure of a reagent holding portion according to a modification of the second embodiment.

The reagent holding portion 323 shown in FIG. 18 has a sixth sheet 3236 and a seventh sheet 3237. The sixth sheet 3236 stores the reagent component 31 inside of a hole. That is, the sixth sheet 3236 is a storage that stores a substance that specifically reacts with a test substance. The seventh sheet 3237 stores the blocking agent B3 inside of a hole. The stacking order of the sixth sheet 3236 and seventh sheet 3237 may be reversed.

Next, an example of the procedure of preparing the reagent holding portion 323 loaded in the injection tool 32 is explained. An example of the procedure of preparing the reagent holding portion 323 as shown in FIG. 16 is explained.

First, a liquid reagent in which the reagent component 31 is dissolved is prepared. A blocking agent B3 is prepared by dissolving a phospholipid such as lecithin in the liquid blocking agent B2. A sheet-like member is prepared as well.

Then, the liquid reagent is applied or sprayed so as to form an even layer on the surface of the prepared member. After moisture of the liquid reagent that has been applied or sprayed is evaporated, the member is turned over, and a liquid including the blocking agent B3 is applied to the reverse surface of the member. Moisture of the applied liquid including the blocking agent B3 is evaporated to dry by a predetermined drying method such as freeze drying. After that, the member is cut into a predetermined size to prepare the fourth sheet 3234. By the above process, the reagent holding portion 323 is prepared.

Next, an example of the procedure of preparing the reagent holding portion 323 as shown in FIG. 17 is explained.

First, a liquid reagent is prepared in which the reagent component 31 is dissolved. A blocking agent B3 is prepared by dissolving a phospholipid in the liquid blocking agent B2. A solution mixture is prepared in which the liquid reagent and the blocking agent B3 are mixed. A sheet-like member is prepared as well.

Then, the solution mixture in which the liquid reagent and the blocking agent B3 are mixed is applied or sprayed so as to form an even layer on the surface of the prepared member. After moisture of the applied or sprayed solution mixture is evaporated to dry, the member is cut into a predetermined size to prepare the fifth sheet 3235. By the above process, the reagent holding portion 323 is prepared. Next, an example of the procedure of preparing the reagent holding portion 323 as shown in FIG. 18 is explained.

First, a liquid reagent is prepared in which the reagent component 31 is dissolved. A blocking agent B3 is prepared by dissolving a phospholipid in the liquid blocking agent B2. A first and second sheet-like members are prepared as well.

Then, the liquid reagent is applied or sprayed so as to form an even layer on the surface of the first member. After moisture of the applied or sprayed liquid reagent is evaporated to dry, the first member is cut into a predetermined size to prepare the sixth sheet 3236.

Then, a liquid which includes the blocking agent B3 is applied or sprayed so as to form an even layer on the surface of the second member. After moisture of the applied or sprayed liquid reagent is evaporated to dry, the second member is cut into a predetermined size to prepare the seventh sheet 3237. The prepared seventh sheet 3237 is stacked onto the prepared sixth sheet 3236. By the above process, the reagent holding portion 323 is prepared.

Next, an example of the procedure in which the blocking agent B3 is dissolved in a test reagent 30 according to the modification is explained below. In the following example, it is assumed that a surfactant is included in an aqueous solution of the test reagent 30.

As shown in FIG. 15, when the user upends the injection device 300 so that the injection tool 32 faces down, the solution mixture in which the aqueous solution and the sample are mixed is brought into contact with the reagent holding portion 323. At the reagent holding portion 323, the solution mixture is brought into contact with the blocking agent B3, and the lipid film of the blocking agent B3 is then dissolved by the surfactant in the solution mixture. When the lipid film is dissolved, the blocking agent B2 covered by the lipid film is dissolved. Next, the solution mixture in which the blocking agent B2 is dissolved is in contact with the reagent component 31, and the reagent component 31 is dissolved in the solution mixture. By this process, the solution mixture including the blocking agent B2 in high concentration is brought into contact with the reagent component 31. Accordingly, the reagent component 31 is exposed to the blocking agent B2 distributed with the high concentration. As a result, nonspecific binding of a test substance A to magnetic particles, in which the first antibody is immobilized, is suppressed.

As stated above, in the modification of the second embodiment, the blocking agent B3 is prepared by covering the blocking agent B2 by the lipid film. The prepared blocking agent B3 is dried and stored in the reagent holding portion 323. By this processing, it is possible to prevent the blocking agent B2 covered by the lipid film of the blocking agent B3 from being dried.

Accordingly, it is possible to prepare the in-vitro diagnostic in which the blocking agent B2 exerts its effects in the liquid state that can be easily preserved, and is expected to realize a high blocking effect with a small amount of a medicinal agent.

While certain embodiments have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the inventions.

The invention claimed is:

1. An in-vitro diagnostic comprising:
   a housing for a liquid comprising a test substance contained in a sample extracted from a subject;
   an optical waveguide as a support;
   a substance layer, on the optical waveguide, that stores a substance that specifically reacts with the test substance and a first blocking agent that supports the substance, wherein the substance is bound to a surface of the optical waveguide; and
   a dry film comprising a soluble coating agent and a second blocking agent separating the housing and the substance layer, wherein the dry film covers a surface of the substance layer, wherein the dry film does not contain a substance that specifically reacts with the test substance, and wherein the second blocking agent is different from the first blocking agent.

2. The in-vitro diagnostic according to claim 1, wherein the second blocking agent is dispersed into a soluble coating agent included in the dry film.

3. The in-vitro diagnostic according to claim 1, wherein the second blocking agent is covered by a lipid film and is dispersed into a soluble coating agent included in the dry film.

4. The in-vitro diagnostic according to claim 1, wherein the second blocking agent is covered by a lipid film and is attached on an upper surface of the dry film.

5. The in-vitro diagnostic according to claim 1, wherein the second blocking agent is selected in accordance with a measurement item.

* * * * *